United States Patent [19]
Morawsky et al.

[11] Patent Number: 5,518,717
[45] Date of Patent: May 21, 1996

[54] HYDROLYZED ZEIN AS HAIR FIXATIVE IN HAIR COMPOSITIONS

[75] Inventors: Natalie Morawsky, Highland Park; Gary T. Martino, Plainsboro, both of N.J.; Jacob Guth, Upper Darby, Pa.; John Tsai, Belle Mead; Roger Jeffcoat, Bridgewater, both of N.J.

[73] Assignee: National Starch and Chemical Investment Holding Corporation, Wilmington, Del.

[21] Appl. No.: 175,838

[22] Filed: Dec. 30, 1993

Related U.S. Application Data

[63] Continuation of Ser. No. 930,866, Apr. 14, 1992, abandoned.

[51] Int. Cl.$^6$ ............... A61K 7/11; A61K 35/78
[52] U.S. Cl. ........... 424/70.14; 424/74; 424/195.1; 424/47; 424/DIG. 1; 132/203
[58] Field of Search ............... 424/70–72, 47, 424/195.1, 70.14, DIG. 1, 74; 132/203

[56] References Cited

U.S. PATENT DOCUMENTS

| | | | |
|---|---|---|---|
| 1,884,015 | 10/1932 | Lougovoy | 424/70.14 |
| 3,370,054 | 2/1968 | Loew | 260/123 |
| 3,842,848 | 10/1974 | Karjala | 132/7 |
| 3,954,725 | 5/1976 | Johnsen et al. | 260/112 R |
| 4,115,548 | 9/1978 | Marsh et al. | 424/70 |
| 4,128,543 | 12/1978 | Johnsen et al. | 260/123.7 |
| 4,229,429 | 10/1980 | Johnsen et al. | 424/47 |
| 4,279,996 | 7/1981 | Yoshioka | 424/72 |
| 4,423,032 | 12/1983 | Abe | 424/71 |
| 4,874,604 | 10/1989 | Sramek | 424/47 |
| 4,897,262 | 1/1990 | Nandagin et al. | 424/71 |
| 4,970,067 | 11/1990 | Panandiker | 424/70 |

FOREIGN PATENT DOCUMENTS

| | | | |
|---|---|---|---|
| 0117469 | 5/1984 | European Pat. Off. | A81K 7/06 |
| 1019013A | 1/1988 | Japan | A61K 7/00 |

OTHER PUBLICATIONS

Brooks Industries, Inc. Product Bulletin, Plant Protein VFGP/2, Spring 1992.
The Merck Index, p. 1596; published 1989.

*Primary Examiner*—Thurman K. Page
*Assistant Examiner*—Sally Gardner
*Attorney, Agent, or Firm*—Eugene Zagarella, Jr.

[57] ABSTRACT

This invention relates to hair fixing compositions containing a natural based hydrolyzed zein fixative which has a selected molecular weight, the composition having low volatile organic compound (VOC) content.

11 Claims, No Drawings

HYDROLYZED ZEIN AS HAIR FIXATIVE IN HAIR COMPOSITIONS

This application is a continuation of application Ser. No. 07/930,866, filed Aug. 14, 1992, now abandoned.

FIELD OF THE INVENTION

This invention relates to the use of natural based hydrolyzed proteins as hair fixatives. More particularly, this invention involves the use of selected hydrolyzed zein derivatives as hair fixatives in compositions having low volatile organic compound (VOC) content.

BACKGROUND OF THE INVENTION

Most hair fixing compositions such as hair setting and hair spray compositions contain a film-forming additive or hair fixative; a solvent, usually alcohol or a mixture of alcohol and water; a fragrance and other additives; and in the case of aerosol products, a propellant. In order to be effective, a hair fixing composition needs to provide hair holding properties, high humidity curl retention, quick drying time, nonstickiness, and a clear, transparent, glossy film which is easily removable by the use of water and/or soap or shampoo. Additionally, the film forming additive must be compatible with the solvents and propellants employed and should be stable in the presence of, and unreactive with, the perfumes or other optional ingredients utilized in the hair setting or hair spray composition.

Various polymeric hair fixative systems have been utilized in an attempt to meet these stringent requirements. However, these systems which usually contain alcohols and a volatile hydrocarbon propellant, are becoming less acceptable because of consumer preference and environmental regulations that limit the amount of volatile organic compounds (VOC) in hair care and other personal care products. In view of these regulations, it is foreseen that water will become a greater component in hair care formulations. Therefore, the cosmetic industry is seeking water soluble or water dispersible polymers which can be used in hair care systems that not only meet the upcoming regulations in providing low VOC content, but also provide the various properties required of such systems as noted previously.

Proteins and hydrolyzed protein have been used in the hair care industry for a number of years. Protein hydrolyzates and other protein derivatives are disclosed as conventional hair spray additives in U.S. Pat. No. 4,874,604 issued Oct. 17, 1989 to J. A. Stramek and U.S. Pat. No. 4,897,262 issued Jan. 30, 1990 to A. Nandagiri et al. Also, they have been used as conditioning agents to improve different hair properties as disclosed in U.S. Pat. No. 4,970,067 issued Nov. 13, 1990 to R. Panandiker et al.

U.S. Pat. No. 4,128,543 issued Dec. 5, 1978 and U.S. Pat. No. 4,229,429 issued Oct. 21, 1980, both to V. Johnson et al., disclose a process for preparing hydrophobically modified hydrolyzed protein, more particularly, collagen for use in anhydrous alcohol hair spray systems. Another U.S. Pat. No. 3,954,725 issued May 4, 1976 to V. Johnson et al. discloses the preparation of acyl amide modified protein hydrolyzates and their use as water-insoluble, alcohol soluble components in cosmetics such as hair sprays.

Despite the prior disclosures noted above, there still exists the need for a water soluble or water dispersible hair fixative that is useful in a range of VOC systems while providing a humidity resistant film with good holding properties that is readily removable from hair with shampoo and water.

SUMMARY OF THE INVENTION

This invention involves a hair fixative composition comprising an effective amount of a hydrolyzed natural based zein fixative in combination with an alcohol-water solvent system.

More particularly, this invention is directed to a hair fixative composition comprising:

a) an effective amount of a hydrolyzed zein fixative, said hydrolyzed zein having a molecular weight of about 3,000 to 20,000;

b) a solvent comprising from about 0 to 85% by weight, based on the weight of the composition, of a polar organic solvent and the balance of the composition water; and c) from about 0 to 60% by weight of a propellant, based on the weight of the composition.

These hair fixative compositions comprising a selected hydrolyzed zein derivative as a fixative are useful over a wide range of volatile organic compound (VOC) content, i.e., 0 to 85% by weight, and especially in the lower amounts that will be mandated by government regulations in the next few years, preferably less than about 80% and more preferably less than about 55% by weight, based on the weight of the composition.

DETAILED DESCRIPTION OF THE INVENTION

The ability to provide a water soluble or water dispersible, natural based hair fixative that is useful and effective in low VOC content hair spray and hair setting compositions is the main feature of this invention. Being able to provide such a water soluble or dispersible film forming fixative is necessary because significant amounts, if not all, of the organic based solvents and propellants found in current hair fixing compositions will be replaced with water to help reduce VOC emissions. While the increased water content makes water solubility or dispersibility a necessity, this is only one of the many requirements that a hair fixative must satisfy. It also must be compatible with hair and other components in the system, provide a humidity resistant, hard, glossy film and be readily removable.

In accordance with this invention a selectively hydrolyzed zein material is provided having the requisite properties of a hair fixative material. This fixative is obtained by hydrolyzing natural based zein to such an extent that the hydrolyzed zein has a molecular weight of from about 3,000 to 20,000, preferably about 5,000 to 15,000 and more preferably about 7,000 to 12,000. In protein chemistry there are many ways to determine molecular weight. In this case, molecular weight was determined by electrophoresis and particularly using the method and conditions disclosed by M. A. Porzio and A. M. Pearson in Biochimica et Biophysica Acta, 490 (1977) 27–34. The hydrolyzed zein has been found to be soluble and/or dispersible in alcohol-water solvent systems and additionally possesses good film forming properties.

Various methods may be used in preparing the hydrolyzed zein, e.g., acid and enzyme hydrolysis. Most desirably, the natural base zein material is hydrolyzed using alkaline hydrolysis. The zein product is prepared by hydrolyzing the starting natural based zein in an aqueous solution of alkali. The alkaline material may be an alkali metal hydroxide such as sodium, potassium or lithium, or calcium hydroxide with sodium hydroxide being preferred. The time required for hydrolysis will depend on the temperature maintained as well as the concentration of the hydrolyzing agent and these and other conditions can be varied until the desired zein hydrolyzate properties, as described above, are attained. Typically, the hydrolysis reaction may be carried out using sodium hydroxide (2 to 25% aqueous solution) along with the zein starting material in a 1:1 to 10:1 ratio by weight of sodium hydroxide solution to zein. The temperature may range from about 40° to 100° C. and reaction time may vary from 2 to 24 hours and more.

After the hydrolysis reaction, the reaction mixture is cooled, the pH adjusted to 7 to 8 and then filtered and the final zein hydrolyzate recovered as the filtrate. Other treatments and modifications may be used to improve some characteristics of the hydrolyzed product if desired. For example, steam stripping, steam distillation, solvent extraction, and treatment with activated carbon are techniques which may be used to improve color and odor of the hydrolyzed zein.

The resulting hydrolyzed zein product, having the molecular weight characteristics as noted previously, is distinguished from regular commercially available zein in that it is fully dispersible or soluble in water and in alcohol-water solvent mixtures, and cast films exhibit good shampoo removability.

The hair fixative compositions of this invention containing hydrolyzed zein also include a solvent system comprising water and a polar organic solvent. While the hydrolyzed zein is dispersible in water, improved dispersibility and solubility will be attained by adding small amounts of organic solvent. The useful solvents are the polar, organic solvents such as alcohols and ketones and especially low boiling alcohols which are compatible with other components in the hair composition system. More particularly, $C_1$ to $C_4$ straight and branched chain alcohols, e.g., ethanol, propanol and isopropanol are useful with ethanol being preferred. Acetone is the preferred ketone which may be used.

The amount of hydrolyzed zein used in the hair fixative compositions of this invention will be an effective fixative amount and more particularly from about 1 to 20% by weight, based on the weight of the composition. Preferably, the hydrolyzed zein will comprise from about 2 to 15% by weight of the composition.

The amount of alcohol or other polar organic solvent used in the water-organic solvent system will be an effective amount to make the hydrolyzed zein readily dispersible or soluble in the formulation. Generally, from about 0 to 85% by weight of solvent, preferably from about 0 to 50 and more preferably from about 0 to 10%, based on the weight of the composition, will be used. The balance of the composition, other than the organic solvent, optional propellant and other additives, will be water. A neutralizing agent, such as amine or alkanolamine, may be used to aid stability by neutralizing any small amount of acidity that may remain. Aminomethyl propanol (AMP) is preferred for this purpose.

The hair fixing composition of this invention may be an aerosol spray containing a propellant. While any of the known propellants may be used in these compositions, preferred propellants include the hydrocarbons, particularly the lower boiling hydrocarbons such as $C_3$–$C_6$ straight and branched chain hydrocarbons, i.e., propane, butane, isobutane and mixtures thereof. Other preferred propellants include the ethers, such as dimethyl ether, hydrofluorocarbons, e.g., 1,1-difluoroethane and the compressed gases such as nitrogen, air and carbon dioxide.

The amount of propellants used in the hair fixing compositions of this invention may vary from about 0 to 60% by weight of the hair spray composition and preferably from about 0 to 40% by weight, based on the weight of the total composition.

An important consideration in determining the amount of organic solvent and propellant to be used in the hair fixative compositions of this invention is the amount of volatile organic compound (VOC) content. While these compositions, containing a selected hydrolyzed zein may have a wide range of VOC content, i.e., from 0 to 85% by weight, it is preferred that there be less than about 80% and more preferably less than about 55% by weight VOC content, based on the weight of the composition.

Optional conventional additives may also be incorporated into the hair fixing composition of this invention in order to modify certain properties thereof. Included among these additives are plasticizers such as glycerine, glycol and phthalate esters; silicones; emollients, lubricants and penetrants such as lanolin compounds; fragrances and perfumes; U.V. absorbers; dyes and other colorants; thickeners; anti-corrosion agents, detackifying agents, combing aids; anti-static agents, preservatives, foam stabilizers, etc. These additives are added in small effective amounts and generally will comprise from about 0.1 to 10% by weight each and from about 0.1 to 20% by weight total, based on the weight of the composition.

The resulting hair fixing compositions exhibit all of the characteristics required of such a product in systems ranging from 0 to 85% VOC. The films found are clear, hard, glossy and provide humidity resistance while being readily removable.

The following examples further illustrate the embodiments of this invention. All parts and percentages are given by weight and all temperatures are in degrees Celsius unless otherwise noted.

EXAMPLE 1

Hydrolyzed zein was prepared in the following manner. An aqueous solution of 3% NaOH was heated to 90° C. and then zein added in a 1.5:1 ratio of alkali solution to zein. The temperature was lowered to 40° C. and the reaction continued overnight (~16 hours) at this temperature. The sample was then neutralized with HCl solution (9.33% concentration) to a pH of 7.5 and then filtered through Whatmann paper and ultrafiltered with a 3,000 MW cut off membrane and the hydrolyzed zein collected and dried.

Similar samples hydrolyzed at 45° C. and 55° C. and using 2:1 NaOH solution:zein for varying lengths of time (6 to 24 hours) were prepared and all were analyzed to determine molecular weight. The molecular weight of the samples were determined by electrophoresis on a density gradient gel (9–18% bisacrylamide) using the sodium dodecyl sulfate (SDS)—polyacrylamide gel electrophoresis technique disclosed by M. A. Porzio and A. M. Pearson in Biochimica et Biophysica Acta, 490 (1977) 27–34. The samples were found to have a molecular weight range of between 7,400 and 11,400.

EXAMPLE 2

Hydrolyzed zein materials prepared as in Example 1 were formulated into the following hair spray formulations.

|  | SYSTEM 1 | SYSTEM 2 | SYSTEM 3 | CONTROL |
|---|---|---|---|---|
| Hydrolyzed zein | 5.0 | 5.0 | 10.0 | — |
| Control[1] | — | — | — | 5.0 |
| Ethanol | 5.0 | 5.0 | 10.0 | — |
| AMP[2] | — | 0.22 | — | 0.96 |
| Dimethyl ether | 30.0 | 30.0 | 30.0 | 30.0 |
| Deionized Water | 60.00 | 59.78 | 50.00 | 64.04 |

[1]film forming polymer of octylacrylamide/acrylates/t-butyl aminoethylmethacrylate
[2]aminomethyl propanol neutralizing agent Each of the above formulations were tested on nine swatches of strands of Remi Blue String European Brown hair for curl retention at 90% relative humidity, 72° F. and the results pooled and averaged. The results are set out in Table 1 and indicate that hydrolyzed formulations effectively retained curl and were slightly better than the control formulation.

TABLE 1

Percentage Curl Retention at 90% relative humidity, 72° F.

|  | SYSTEM 1 | SYSTEM 2 | SYSTEM 3 | CONTROL |
|---|---|---|---|---|
| 0.25 Hour | 88.6 | 90.6 | 87.6 | 84.4 |
| 0.5 Hour | 87 | 88.9 | 83.6 | 81.9 |
| 1.0 Hour | 84 | 83 | 75.9 | 74.1 |
| 1.5 Hour | 82.9 | 80.9 | 75.1 | 73.4 |
| 2.0 Hour | 82.6 | 80.9 | 74.3 | 71 |
| 3.0 Hour | 82.6 | 80.2 | 70.2 | 68.7 |
| 4.0 Hour | 79.7 | 79.5 | 69.4 | 66.4 |
| 5.0 Hour | 79.7 | 77.1 | 69.4 | 65.6 |
| 24.0 Hour | 66.9 | 71.1 | 61.9 | 58 |

EXAMPLE 3

The tack and drying time of hydrolyzed zein containing aerosol compositions were compared to that of the control identified in Example 2. The zein based aerosols had 5 and 7.5% solids, each containing 30% DME (dimethyl ether) and the balance water. Results were as follows:

| TEST AEROSOL | CONTROL AEROSOL | TACK TIME | DRY TIME |
|---|---|---|---|
| 5% hydrolyzed zein | 5% aqueous Control | = | = |
| 7.5% hydrolyzed zein | 5% aqueous Control | + | + |

+: test sample is significantly superior to control
−: test sample is significantly inferior to control
=: no significant difference (95% confidence level)

Although the zein composition did not dry more quickly on an equal solids basis, it dried significantly more quickly with less tack at increased solids.

Other subjective evaluations showed the hydrolyzed zein containing compositions as compared with the control resulted in a stiffer film with no significant differences noted in gloss, dry combability, flake and static dissipation.

EXAMPLE 4

Hydrolyzed zein prepared as in Example 1 was formulated into the following non-aerosol hair spray formulation:

| Ingredients | Weight % |
|---|---|
| Hydrolyzed zein | 10.0 |
| Acetone | 45.0 |
| Deionized water | 45.0 |

The hydrolyzed zein was added to the solvents under agitation, resulting in a stable dispersion of the zein product in the solvent medium. The formula was tested against RAVE® 3 (Ultra Hold), a commercial non-aerosol hair spray containing the synthetic fixative polymer octylacrylamide/acrylates/butylaminoethyl methacrylate copolymer. The hydrolyzed zein based formulation showed parity in stiffness, flake and static dissipation compared to the commercial product and superiority in gloss and dry combability.

EXAMPLE 5

A mousse composition containing hydrolyzed zein prepared as in Example 1 was formulated as follows:

| Ingredients | Weight |
|---|---|
| Part A |  |
| Ethanol | 50.0 |
| Emulsifying wax (NF) | 1.0 |
| Part B |  |
| Cetrimonium chloride | 0.50 |
| Steareth-21 | 0.50 |
| Nonoxynol-40 | 1.50 |
| Deionized water | 37.0 |
| Hydrolyzed zein | 5.0 |
| Part C |  |
| n-butane | 2.25 |
| Propane | 2.25 |

Part A and Part B were dissolved separately. Once both portions were homogeneous, Part B was added to Part A while under agitation and stirred until the mixture was homogeneous. Part C, the propellants, was added to the mixture and formed the mousse product which gave a rich, stable foam. The properties of the mousse, as tested against untreated hair, showed that the mousse imparted significantly superior wet combing, gloss, stiffness, dry combing and static dissipation to the hair. A second test was run comparing the mousse formulation with and without hydrolyzed zein to track the properties attributed to zein. The sample formulation with the hydrolyzed zein demonstrated significantly more stiffness and significantly better dry combability.

What is claimed is:

1. A hair fixative composition which provides hair holding properties at 90% humidity, curl retention and is removable with water, shampoo or soap consisting essentially of:
   a) from 1 to 10% by weight, based on the weight of the composition, of hydrolyzed zein having a molecular weight of from 7,000 to 11,400;
   b) from about 0. to 85% by weight, based on the weight of the composition, of a solvent system comprising a polar organic solvent selected from the group consisting of $C_1$ to $C_4$ alcohols and ketones;

c) from about 0 to 60% by weight, based on the weight of the composition, of a propellant; and d) the balance of the composition water.

2. A method for providing hair with hair holding properties at 90% humidity, curl retention and removability with water, shampoo or soap comprising contacting the hair with an effective amount of a hair fixative composition consisting essentially of:

a) from 1 to 10% by weight, based on the weight of the composition of hydrolyzed zein having a molecular weight of from 7,000 to 11,400;

b) from about 0 to 85% by weight, based on the weight of the composition, of a solvent system comprising a polar organic solvent selected from the group consisting of $C_1$ to $C_4$ alcohols and ketones;

c) from about 0 to 60% by weight, based on the weight of the composition, of a propellant; and d) the balance of the composition water.

3. The composition of claim 1 wherein there is a VOC content of less than about 80% by weight, based on the weight of the composition.

4. The composition of claim 3 wherein the polar organic solvent is an alcohol.

5. The composition of claim 3 wherein the polar organic solvent is acetone.

6. The composition of claim 4 wherein from about 0 to 50% by weight, based on the weight of the composition, of said alcohol is used.

7. The composition of claim 6 wherein there is a VOC content of less than about 55% by weight, based on the weight of the composition.

8. The composition of claim 6 wherein said alcohol is a $C_1$ to $C_4$ straight or branched chain alcohol.

9. The composition of claim 8 wherein the alcohol is ethanol.

10. The composition of claim 9 wherein there is a VOC content of less than about 55% by weight, based on the weight of the composition.

11. The method of claim 2 wherein the hair fixative composition has a VOC content of less than about 80% by weight, based on the weight of the composition.

\* \* \* \* \*